United States Patent
García-España Monsonís et al.

(10) Patent No.: US 9,750,677 B2
(45) Date of Patent: Sep. 5, 2017

(54) USE OF METAL COMPLEXES WHICH ARE MIMETICS OF SOD AS FOOD AGENTS AND AS COSMETICS

(71) Applicant: Universitat de València, Valencia (ES)

(72) Inventors: Enrique García-España Monsonís, Valencia (ES); María Paz Clares García, Valencia (ES); Salvador Blasco Llopis, Valencia (ES); Concepción Soriano Soto, Valencia (ES); Jorge González García, Valencia (ES); Begoña Verdejo Viu, Valencia (ES)

( * ) Notice: Subject to any disclaimer, the term of this patent is extended or adjusted under 35 U.S.C. 154(b) by 0 days.

(21) Appl. No.: 15/121,030

(22) PCT Filed: Feb. 24, 2015

(86) PCT No.: PCT/ES2015/070125
§ 371 (c)(1),
(2) Date: Aug. 23, 2016

(87) PCT Pub. No.: WO2015/124824
PCT Pub. Date: Aug. 27, 2015

(65) Prior Publication Data
US 2017/0007521 A1    Jan. 12, 2017

(30) Foreign Application Priority Data
Feb. 24, 2014 (ES) .................. 201400148

(51) Int. Cl.
| | | |
|---|---|---|
| *A61K 8/18* | (2006.01) | |
| *A61K 31/555* | (2006.01) | |
| *A61K 8/49* | (2006.01) | |
| *C07D 471/08* | (2006.01) | |
| *A61Q 19/00* | (2006.01) | |
| *A61K 8/19* | (2006.01) | |
| *A23L 5/00* | (2016.01) | |
| *A23L 33/16* | (2016.01) | |

(52) U.S. Cl.
CPC ............ *A61K 8/494* (2013.01); *A23L 5/00* (2016.08); *A23L 33/16* (2016.08); *A61K 8/19* (2013.01); *A61Q 19/00* (2013.01); *C07D 471/08* (2013.01); *A23V 2002/00* (2013.01); *A61K 2800/10* (2013.01); *A61K 2800/522* (2013.01); *A61K 2800/58* (2013.01)

(58) Field of Classification Search
CPC .......... A61K 8/18; A61K 8/49; A61K 31/555
USPC ................... 424/401, 439, 639; 514/185
See application file for complete search history.

(56) References Cited

U.S. PATENT DOCUMENTS

| | | | |
|---|---|---|---|
| 6,794,371 | B1 | 9/2004 | Frank |
| 9,145,386 | B2* | 9/2015 | Garcia-Espana Monsonis ............ C07D 401/12 |
| 2007/0298354 | A1 | 12/2007 | Ding et al. |
| 2013/0287696 | A1 | 10/2013 | Salvemini et al. |

FOREIGN PATENT DOCUMENTS

| | | |
|---|---|---|
| EP | 2113242 A1 | 11/2009 |
| ES | 2355784 B1 | 3/2011 |
| ES | 2414291 A1 | 7/2013 |

OTHER PUBLICATIONS

Campana, F.; Zervoudis, S. et al.; 2004, "Topical superoxide dismutase reduces post-irradiation breast cancer fibrosis," J Cell Mol Med, Jan-Mar; 8(1):109-16.
Glares, M.P. et al.; "Manganese(II) complexes of scorpiand-like azamacrocycles as MnSOD mimics," Chem. Commun., 2011,47, 5988-5990.

* cited by examiner

*Primary Examiner* — Charanjit Aulakh
(74) *Attorney, Agent, or Firm* — Moore Patents; David Dreyfuss

(57) ABSTRACT

This invention relates to the use of the metal complexes which are mimetics of the superoxide dismutase (SOD) enzyme produced from macrocyclic polyazapyridinophane compounds of formula (1) as food agents and also as cosmetics.

10 Claims, 1 Drawing Sheet

USE OF METAL COMPLEXES WHICH ARE MIMETICS OF SOD AS FOOD AGENTS AND AS COSMETICS

FIELD OF THE INVENTION

The present invention refers to the use of metal complexes mimetic of the enzyme superoxide dismutase (SOD), described in patent ES2355784 and obtained from macrocyclic polyazapyridinophane compounds, as food agents and for their use as cosmetics.

STATE OF THE ART

Antioxidants play an important role in skin protection and repair mechanisms. They may be consumed as food or as food supplements, or may be applied on the skin as topical formulations. The enzyme superoxide dismutase (SOD) belongs to the most important group of natural antioxidant substances.

Prior art reflects that SOD performs important functions in the body such as, for example, protecting against cellular oxidative stress and against inflammatory or degenerative processes. The dismutation reaction of the superoxide radical ($O_2^-$) into oxygen and hydrogen peroxide ($H_2O_2$), catalysed by the SOD enzyme, makes this enzyme very important in antioxidant defence for the majority of cells exposed to oxygen. Thus, SOD protects the cell from the harmful reactions of the $O_2^-$ radical.

When SOD activity fails, there is an increase in oxidative stress that leads to the development of various disorders or diseases in the human body such as, for example, inflammatory processes, carcinogenic processes or degenerative processes.

Although the underlying mechanism of the action of these substances is not known in detail, there are enough studies on the distribution, activity and regulation of antioxidants to enable the development of action strategies from the point of view of nutrition and cosmetics that involve new antioxidant formulations. These new projects include reduction of cancer risk induced by UV light, ageing caused by the action of light, prevention and treatment of diseases that cause skin peeling as well as maintenance of good health and amelioration of the effects of ageing.

Some plants produce SOD naturally, such as broccoli, wheat and barley, but when SOD is ingested by the human body it is quickly destroyed by the stomach acids and intestinal enzymes, so it scarcely reaches the bloodstream. Furthermore, the human body has a maximum peak of production of SOD at the approximate age of 10 years. It is possible to raise blood levels of SOD by consuming supplements of suitable precursor molecules in appropriate amounts. It is also known that wheat sprouts are a rich source of these precursors. However, the same problem of SOD destruction by the digestive process remains.

Therefore, the synthesis of compounds mimetic of the SOD enzyme is necessary to compensate for the possible deficiencies or absence of endogenous SOD activity and so to be able to treat, not only the numerous pathologies or diseases with a common aetiology of lack or deficient activity of this enzyme, but also to make use of their ability as food or cosmetic agents. Ideally, synthesised mimetic compounds must have low toxicity and also be capable of performing the dismutation reaction with the lowest possible concentration of the compound. The use of lower concentrations or doses of SOD mimetics would reduce treatment cost as well as the risk associated with development of side effects and immunogenicity.

The use of SOD in cosmetic products is known to reduce the harm of free radicals in the skin, for example to reduce fibrosis that is caused as a consequence of radiotherapy. The main patent ES2355784 already mentions bibliography related to this effect. A more recent study also related to the cosmetic effect is Campana F., Zervoudis S. et al., 2004. *Topical superoxide dismutase reduces post-irradiation breast cancer fibrosis. J Cell Mol Med.* January-March; 8(1):109-16. A mechanism that could explain the effect of SOD as an agent able to reverse fibrosis is the possible reversion of myofibroblasts back to fibroblasts.

An example of an SOD mimetic used as a cosmetic is lipocromano-6 (EP2113242) or the one described in patent application US20130287696, which discloses a method for preventing deterioration and oxidation of foods by the application of an effective amount of a pegylated SOD mimetic, optionally in combination with a second preserving additive. A specific example of a SOD mimetic of this patent is that shown below:

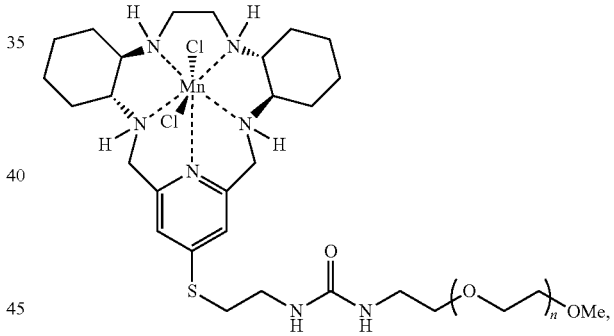

VII

It is also known that SOD is taken orally to remove wrinkles or rebuild tissue, but there is no evidence that these products taken orally are absorbed by the body.

No document has been found in the state of the art that specifically discloses metal complexes developed in the main patent ES2355784. Therefore, neither their uses as cosmetics nor as food agents have been disclosed.

Metal complexes described in the main patent have low toxicity, low values of $IC_{50}$ and do not cause the development of immunogenicity. The low value of the $IC_{50}$ of these metal complexes has important implications because the lower this value, the lower is the amount of compound necessary to cause the desired mimetic effect. Therefore the use of a lower amount of the complex to achieve the dismutation reaction would considerably reduce the side effects.

Furthermore, the aforementioned metal complexes have a long half-life because of their stability in plasma and they do not show problems in tissue distribution after administration.

DESCRIPTION OF THE INVENTION

This invention refers to the use of metal complexes, mimetic of SOD, obtained from intermediary macrocyclic polyazapyridinophane compounds with a heterocyclic quinoline linked to the central structure of the molecule, as already described in ES2355784, as cosmetics or as food agents.

The term "food agent" in this document relates any of the following alternatives: food additive, functional food, dietary supplement or functional drink.

A metal complex relates in this document to any molecular association of the intermediary compounds of Formula 1, with at least one metal ion, preferably Cu(II), Fe(II) or Mn(II), and more preferably where the metal ion is Mn(II).

Formula 1

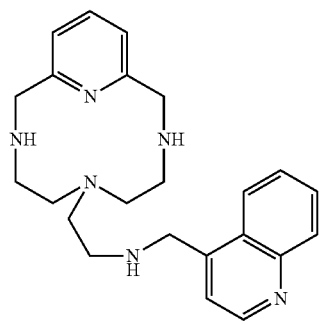

(1)

In present invention, an SOD mimetic complex relates to a metal complex capable to imitate, supplement and eventually to improve the activity and/or functions of the endogenous SOD enzyme as a cosmetic, personal hygiene product or food agent.

Metal complexes described in ES2355784 may be included in formulations for food or cosmetic use and administered in accordance with known techniques of the state of the art in various ways such as intradermal injection or orally via capsules, dragees or tablets.

As formulations for cosmetic use or personal hygiene products they may form part of deodorants, antiperspirants, hair and skin care products, and may be, for example, moisturizers, cleansing products or combinations of both. Formulations for cosmetic use or personal hygiene products may also be in the form of powders or solid bars or other solid forms such as, for example, creams, milks, lotions, emulsions, pastes, liquids, gels, aerosols, solid forms, jellies, ointments, masks, dispersions, suspensions, shampoos, foams, sprays or anhydrous liquids.

Similarly, solid forms for cosmetic use can be made in the presence of the necessary excipients selected from the group comprising, but not limited to, mannitol, polyvinylpyrrolidone, microcrystalline cellulose, silica gel, talc, magnesium stearate, titanium oxide, dyes and antioxidants.

Thus the invention refers more specifically to the use as a cosmetic or food agent of a metal complex mimetic of superoxide dismutase of Formula 1

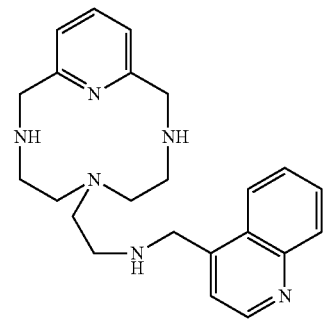

(1)

with at least one metal ion. The metal ion is preferably selected from Cu(II), Fe(II) and Mn(II), and more preferably is Mn (II).

This invention also refers to the use of metal complexes mimetic of SOD of Formula 1 with at least one metal ion for the preparation of a food agent, which may be a food additive, functional food, dietary supplement or functional drink, or for the preparation of a personal hygiene product or cosmetic formulation. The metal ion is preferably selected from Cu(II), Fe(II) and Mn(II), and more preferably is Mn(II).

In addition, present invention refers also to a cosmetic formulation or personal hygiene product that comprises at least one metal complex mimetic of SOD of Formula 1 with at least one metal ion, as defined above.

This cosmetic formulation or personal hygiene product may be formulated as a cream, paste, milk, gel, lotion, ointment, suspension, dispersion, powder, shampoo, foam, spray or solid bar.

Also, present invention relates to a food additive, dietary supplement, functional food or functional drink which comprises at least a metal complex mimetic of SOD of Formula 1 with at least one metal ion, as defined above.

Metal complexes of the invention overcome the problems listed in the state of the art because they have reduced toxicity and low $IC_{50}$ values. The low $IC_{50}$ of metal complexes of this invention have important implications because the lower this value, the smaller is the amount of complex necessary to cause the desired mimetic effect. Therefore, the use of a smaller amount of complex to achieve the dismutation reaction considerably reduces the side effects.

In addition, metal complexes of the invention have high stability, as shown in the main patent ES2355784, and half-life, avoiding distribution problems in tissues after administration as well as the development of immunogenicity.

A preferred embodiment of the invention refers to the use of mimetic compounds in which the metal ions are bound to the compound of Formula 1 are selected from Cu(II), Fe(II) and Mn(II).

EXAMPLE

1. Materials and Methods

1.1 Medaka Embryos

Figure 1:
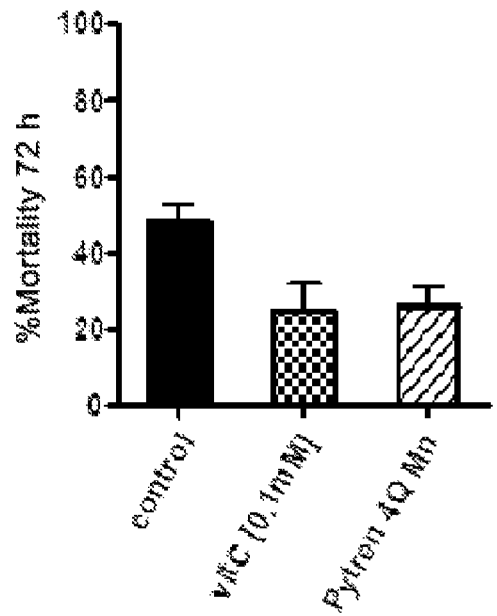
FIG. 1: Graphical representation of the results obtained after incubation of Medaka embryos in stage 8 with the oxidant $H_2O_2$ and the compound Pytren-4Q+Mn for 72 hours, as detailed in the example.

Individual adults (strain Cab, Carolina Biological Supply, (North Carolina)), were held in tanks with continuous water flow at 27° C., and a photoperiod of 14 hours of light and 10 hours of darkness. The fish were fed twice a day with *Artemia nauplii*, which were hatched daily from commercial Sanders® cysts, and with dry food once per day.

Fertilized eggs were collected daily, deposited in Yamamoto solution (0.13 M NaCl, 2.7 mM KCl, 1.8 mM CaCl2 and 0.24 mM $NaHCO_3$, pH 7.3) (Yamamoto T., Medaka (killifish): Biology and strains. 1975, Tokyo: Keigaku Pub. Co), and were kept in the incubator at 26° C. The embryo stage was determined according to the description of Iwamatsu (Iwamatsu T., Stages of normal development in the medaka *Oryzias latipes*. Mech Dev. 2004, Vol. 121, pages 605-618).

1.2 Survival Analysis Using Medaka Fish Embryos

Medaka embryos that were in stage 8 (early morula stage, Iwamatsu, 2004) were separated into 2 groups of 60 embryos and one group of 30 embryos. A group of 60 embryos were treated for 4 days with Pytren-4Q+Mn dissolved in Yamamoto solution at a concentration of 250 µM. The other group of 60 embryos were incubated for 4 days in Yamamoto solution. This group was used as a negative control. The group of 30 embryos, positive control group, were treated for 4 days with a Yamamoto solution of vitamin C, an antioxidant compound, at a concentration of 100 µM. After 4 days of incubation, the embryos were washed with Yamamoto solution. The groups of 60 embryos were separated one by one into two groups of 30 embryos. The embryos of all the groups were individually placed into the wells of 96-well plates, each well containing 200 µl of Yamamoto solution with $H_2O_2$, at different concentrations depending on the extension of incubation time at which mortality was observed. When mortality was observed at 72 hours after being placed in $H_2O_2$ Yamamoto solution, the concentration of $H_2O_2$ used was 22.5 mM. Thirty embryos of each initial group of 60 embryos and the 30 embryos of the group treated with vitamin C were treated with $H_2O_2$ Yamamoto solution at a concentration of 22.5 mM. When mortality was observed at 14 days after being placed in $H_2O_2$ Yamamoto solution, the concentration of $H_2O_2$ used was 7.5 mM. Thirty embryos of each initial group of 60 embryos were treated with $H_2O_2$ Yamamoto solution at a concentration of 7.5 mM. This experiment was replicated in its totality 6 times in the test at 72 hours and 3 times in the test of 14 days.

1.3 Statistical Analysis

To evaluate survival differences when comparing the 3 test groups, the statistical test for one-way analysis of variance (ANOVA) was applied to determine if there were statistically significant differences. Subsequently, Tukey's post-hoc test was applied to establish which of the 3 groups had statistically significant differences. When 2 test groups were compared, the statistical Students t-test was applied. The level of significance was set at $p<0.05$ in all cases. All these analyses were performed using the GraphPad Prism 5.0a program.

2. Results

Figure 2:
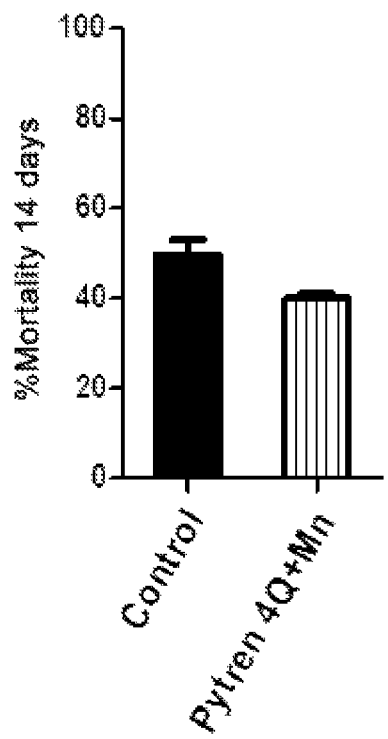
FIG. 2: Graphical representation of the results obtained after incubating Medaka embryos in stage 8 with the oxidant $H_2O_2$ and the compound Pytren-4Q+Mn for 14 days, as described in the example.

Tests were performed with compound Pytren-4Q+Mn at a non-toxic concentration for the embryos of 250 µM and their antioxidant capacity was measured in two different assays. The first test measured mortality after 72 h incubation with 22.5 µM $H_2O_2$ (shown in FIG. 1). The second test measured mortality after 14 days incubation with 7.5 mM $H_2O_2$ (shown in FIG. 2). Both tests showed a significant reduction in mortality in response to oxidative stress caused by $H_2O_2$. The test performed at 72 hours showed that both Pytren-4Q+Mn and vitamin C reduced mortality, which was 48.44±4.40% in the control and 24.96±7.11% in the embryos treated with Pytren-4Q+Mn, and 25.99±5.25% in the embryos treated with vitamin C (Table 1). Therefore the compound of the invention Pytren-4Q+Mn exerts an antioxidant activity similar to that of vitamin C at the tested concentrations.

TABLE 1

Data obtained in the tests of the example of the invention at 72 hours of incubation.

| 72 hours | Control | Pytren-4Q + Mn | Vitamin C |
|---|---|---|---|
| Replicate 1 | 62.5 | 50 | 40.63 |
| Replicate 2 | 56.25 | 43.75 | 43.75 |
| Replicate 3 | 50 | 12.9 | 15.63 |
| Replicate 4 | 43.75 | 15.63 | 14.3 |
| Replicate 5 | 46.9 | 18.75 | 20.8 |
| Replicate 6 | 31.25 | 8.7 | 20.8 |
| Mean | 48.44 | 24.96 | 25.99 |
| Standard deviation | 10.78 | 17.41 | 12.87 |
| Standard error | 4.40 | 7.11 | 5.25 |

The test performed at 14 days showed that Pytren-4Q+Mn reduced mortality, which was 51.27±3.12% in the control, 41.47±1.52% in the embryos treated with Pytren-4Q+Mn (Table 2). The main differences reside in the fact that the detection at 14 days although longer, it is more sensitive because small lethal effects can be detected later.

TABLE 2

Data obtained in the tests of the example of the invention at 14 hours of incubation.

| 14 days | Control | Pytren-4Q + Mn |
|---|---|---|
| Replicate 1 | 46.9 | 39.3 |
| Replicate 2 | 57.3 | 40.7 |
| Replicate 3 | 49.6 | 44.4 |
| Mean | 51.27 | 41.47 |
| Standard deviation | 5.40 | 2.64 |
| Standard error | 3.12 | 1.52 |

The data obtained show that the compound Pytren-4Q+Mn has antioxidant properties at a concentration of 250 µM, similar to that of vitamin C at 100 µM.

The invention claimed is:

1. A cosmetic formulation comprising a metal complex mimetic of superoxide dismutase of Formula 1 with at least one metal ion

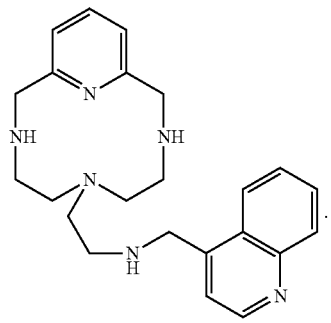

2. A food agent comprising a metal complex mimetic of superoxide dismutase of Formula 1 with at least one metal ion (1)

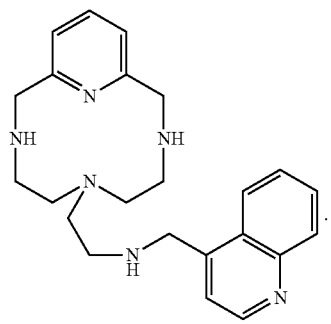

3. The cosmetic formulation of claim 1, wherein the metal ion comprises Cu(II), Fe(II) or Mn(II).

4. The cosmetic formulation of claim 3, wherein the ion is Mn(II).

5. The food agent of claim 2, wherein the food agent is a food additive, dietary supplement, functional food or functional drink.

6. A personal hygiene product comprising a metal complex mimetic of superoxide dismutase of Formula 1 with at least one metal ion (1)

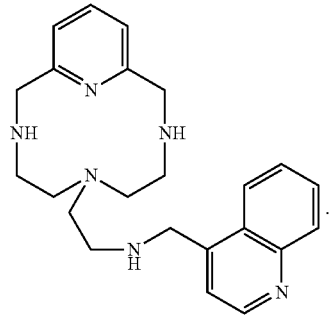

7. The cosmetic formulation of claim 1, wherein said formulation is formulated as a cream, paste, milk, gel, lotion, ointment, suspension, dispersion, powder, shampoo, foam, spray or solid bar.

8. The food agent of claim 2, wherein the metal ion comprises Cu(II), Fe(II) or Mn(II).

9. The food agent of claim 8, wherein the ion is Mn(II).

10. The personal hygiene product of claim 6, wherein the cosmetic formulation is formulated as a cream, paste, milk, gel, lotion, ointment, suspension, dispersion, powder, shampoo, foam, spray or solid bar.

* * * * *